United States Patent
Teichman (10) Patent No.: US 7,804,604 B2
(45) Date of Patent: Sep. 28, 2010

(54) IN-FLIGHT DROP LOCATION VERIFICATION SYSTEM

(75) Inventor: Eyal Teichman, Hod-Hasharon (IL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/045,046

(22) Filed: Mar. 10, 2008

(65) Prior Publication Data

US 2008/0220174 A1 Sep. 11, 2008

Related U.S. Application Data

(63) Continuation of application No. 11/253,425, filed on Oct. 19, 2005, now Pat. No. 7,342,670.

(51) Int. Cl.
*G01B 11/14* (2006.01)

(52) U.S. Cl. ...................... 356/614; 356/616

(58) Field of Classification Search ............ 118/24; 347/19, 20, 29, 47, 74, 81, 100; 356/614–619; 427/8–10, 19

See application file for complete search history.

(56) References Cited

U.S. PATENT DOCUMENTS

| 4,391,518 | A | 7/1983 | Owen et al. |
| 6,213,354 | B1 | 4/2001 | Kay |
| 7,262,785 | B2 | 8/2007 | Silverman et al. |
| 2001/0050294 | A1 | 12/2001 | Plattner et al. |
| 2003/0003220 | A1 | 1/2003 | Zhong et al. |
| 2003/0207019 | A1 | 11/2003 | Shekalim et al. |
| 2005/0122363 | A1* | 6/2005 | Koyama ............ 347/19 |

FOREIGN PATENT DOCUMENTS

| DE | 19809789 A1 | 9/1999 |
| FR | 1 588 650 A | 4/1970 |
| GB | 2365523 A | 2/2002 |
| JP | 11/051612 * | 2/1999 |
| WO | WO99/44037 A | 9/1999 |
| WO | WO 01-91918 A1 | 12/2001 |
| WO | WO02/11065 A2 | 2/2002 |
| WO | WO02/31182 A2 | 4/2002 |
| WO | WO2004/026182 A2 | 4/2004 |

OTHER PUBLICATIONS

Oxford Lasers Imaging Divisions, Do You Image Sprays? www.oxfordlasers.com.
Oxford Lasers Imaging Divisions, In-Flight Sizing Instruments www.oxfordlasers.com.
Oxford Lasers Imaging Divisions, Drop Sizing Software www.oxfordlasers.com.

* cited by examiner

*Primary Examiner*—Tarifur Chowdhury
*Assistant Examiner*—Tara S Pajoohi
(74) *Attorney, Agent, or Firm*—Vidas, Arrett & Steinkraus P.A.

(57) ABSTRACT

A system measures a location of a drop delivered by, for example, an ink-jet type applicator. An image of the drop is captured from two directions, resulting in two drop images. Only one image capturing apparatus is needed to capture the drop images. The location in three-dimensional space is determined by using the two images but only one image capturing device. The position or location information can then be used to calibrate a coating apparatus.

16 Claims, 8 Drawing Sheets

IN-FLIGHT DROP LOCATION VERIFICATION SYSTEM

FIELD OF THE INVENTION

The present invention is directed toward a system to measure a location of a drop delivered by, for example, an ink-jet type applicator. A location in three-dimensional space is determined by capturing two images. The location information can then be used to calibrate a coating apparatus.

BACKGROUND OF THE INVENTION

The benefits of delivering drug-loaded prostheses to patients are becoming well known. Studies have shown the effectiveness of delivering the correct drug dose density on coronary stents to prevent restenosis by application of, for example, paclitaxel or rapamycin. Numerous processes have been proposed for the application of such a coating including: soaking or dipping the implantable device in a bath of liquid medication, soaking in an agitated bath, introducing heat and/or ultrasonic energy in conjunction with a medicated bath, and spraying the medication by way of pressurized nozzles.

It is known to use ink-jet technology to apply a liquid to selected portions of a surface of a medical device such as a stent. An ink-jet nozzle moves with respect to the surfaces of the stent to be coated with the aid of a motion control system. In one configuration, the ink-jet nozzle moves along a linear track over the surface of the stent. The stent is rotated in order to present the surface to the ink-jet nozzle. The combination of the rotatable stent and the movable ink-jet nozzle allows for coating to be placed almost anywhere on the surface of the stent.

As the coating must be precisely applied, there are various known methods for controlling the accuracy of the coating placement so that only the stent is coated and not other parts. A real-time picture can be taken with a camera to determine the position of the ink-jet nozzle in relation to the prosthesis. Based upon the feedback of nozzle location, the ink-jet applicator can be controlled by coordinating the activation of the spray with the movement of the ink-jet nozzle, and/or with the movement of the prosthesis. The accuracy of the coating apparatus is a key to its successful operation.

SUMMARY OF THE INVENTION

A system is provided to allow for correction or adjustment of the positioning characteristics of an ink jet applicator in a medical device coating apparatus.

In one embodiment, a drop position detecting apparatus includes a first light source oriented to provide a first light in a first direction; a second light source oriented to provide a second light in a second direction; the first and second light sources oriented substantially in a first plane, the first plane oriented substantially orthogonal to a predetermined flight path of a drop; a beam splitter having first and second portions; a first mirror, positioned to receive the first light, the first mirror to reflect the received first light to the first portion of the beam splitter; and a second mirror, positioned to receive the second light, the second mirror to reflect the received second light to the second portion of the beam splitter. In another embodiment, a method of detecting a location of a drop in-flight traveling in a flight path comprises: capturing, from a first position, a first drop image of the drop; and capturing, from a second position, a second drop image of the drop, wherein the first and second positions are substantially co-planar, the plane being substantially orthogonal to the flight path, and wherein the first and second drop images are captured substantially at a same time.

In another embodiment, a method of detecting an in-flight location of a drop traveling in a flight path, the drop having been ejected from an applicator in a coating system, comprises: capturing, from a first position, a first drop image of the drop; capturing, from a second position, a second drop image of the drop, wherein the first and second positions are substantially co-planar, the plane being substantially orthogonal to the flight path, and the first and second positions are substantially perpendicular to one another with respect to the flight path.

In another embodiment, a method of determining positioning accuracy of an ink jet applicator in a coating system comprises: positioning the ink jet applicator at a predetermined location; ejecting a plurality of drops from the ink jet applicator; for each of one or more of the plurality of ejected drops: capturing, from a first position, a first drop image; and determining a first drop coordinate of the drop in the first drop image; determining an average first drop coordinate from the one or more determined first drop coordinates; for each of one or more of the plurality of ejected drops: capturing, from a second position, a second drop image; and determining a second drop coordinate of the drop in the second drop image; determining an average second drop coordinate from the one or more determined second drop coordinates; comparing the average first drop coordinate to a predetermined first drop coordinate to determine a first coordinate difference value therebetween; determining whether or not the first coordinate difference value exceeds a first coordinate threshold difference value; comparing the average second drop coordinate to a predetermined second drop coordinate to determine a second coordinate difference value therebetween; and determining whether or not the second coordinate difference value exceeds a second coordinate threshold difference value, wherein, if the first coordinate difference value does not exceed the first coordinate threshold difference value and the second coordinate difference value does not exceed the second coordinate threshold difference value, adjusting at least one coating system parameter as a function of at least one of the first and second coordinate difference values.

BRIEF DESCRIPTION OF THE DRAWINGS

The above and further advantages of the invention may be better understood by referring to the following description in conjunction with the accompanying drawings in which:

FIGS. 2-A and 2-B are graphs representing the locations of successive drops in an X,Z coordinate system;

FIGS. 4-A and 4-B are schematic views of a position detecting system according to different embodiments of the present invention;

FIGS. 6-A-6-C are examples of images captured by an image capturing device in the system shown in FIG. 4-A;

DETAILED DESCRIPTION

Coating an implantable device, for example, a stent, requires the precise application of coating material on extremely small surfaces. The coating application system's positioning accuracy must be maintained or the coating may be incompletely applied or, worse yet, deposited in a location that compromises the integrity of the stent.

A system will be described that facilitates the calibration of an ink-jet applicator as used to coat a stent. The locations of drops ejected by an ink-jet applicator are determined in two dimensions using only one image capturing device. The drop location verification system of the present invention is applicable to maintaining the positional accuracy of the coating applicator during the operating lifecycle of the coating apparatus.

The invention is herein described, by way of example only, with reference to the accompanying drawings. It is stressed that the particulars shown are by way of example and for purposes of illustrative discussion of the various embodiments of the present invention only, and are presented in the cause of providing, what is believed to be, the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Prior to explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for the sake of clarity, described in the context of separate embodiments, may also be provided in combination in a single embodiment. Conversely, various features of the invention, which are, for brevity, described in the context of a single embodiment, may also be provided separately or in any suitable subcombination.

Figure 1:
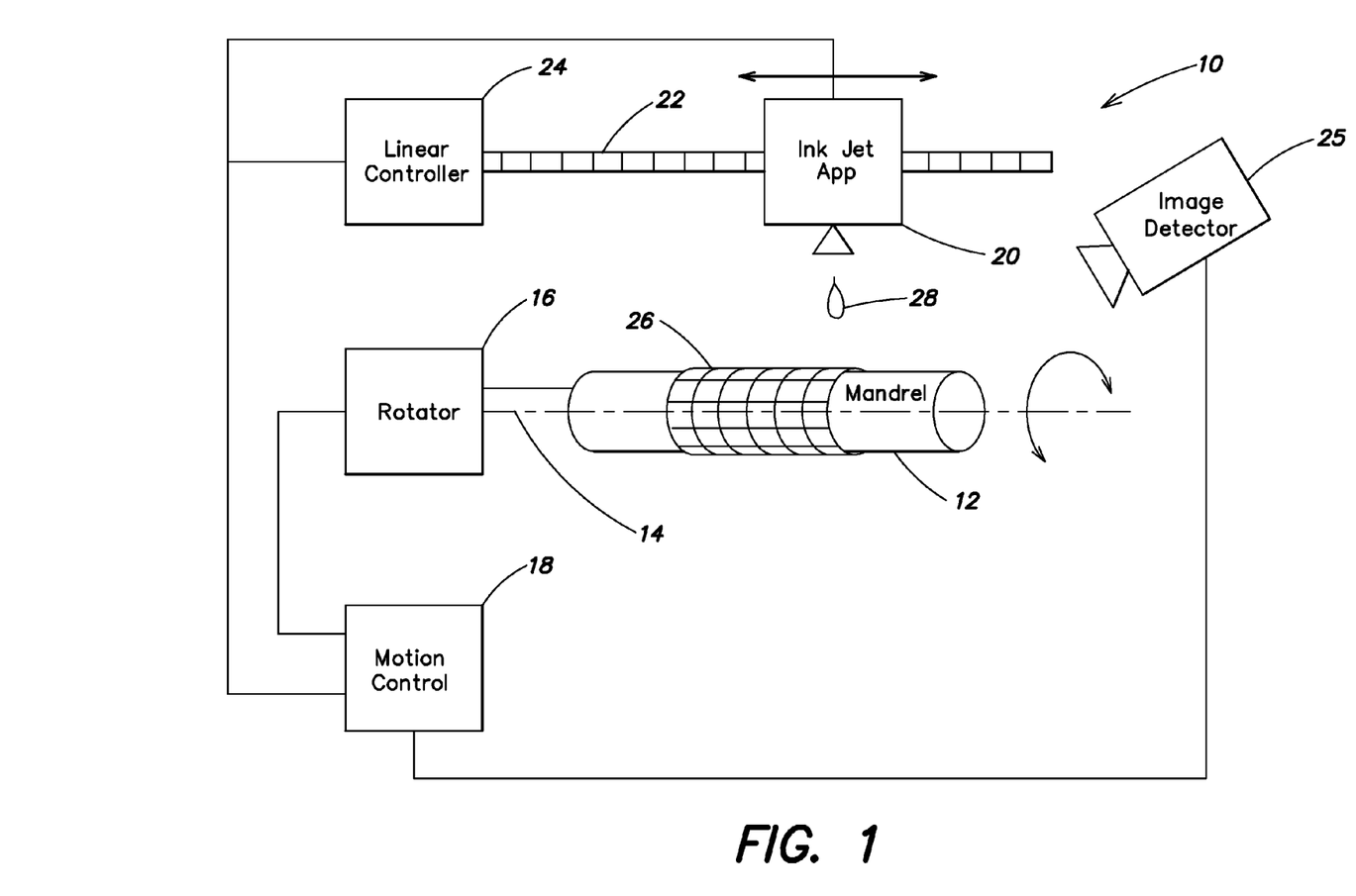
FIG. 1 is a schematic view of a stent coating system.

A coating application system 10, generally shown in FIG. 1, includes a mandrel 12 on a rotating axis 14 coupled to a rotator 16 operating under the control of a motion control system 18. An inkjet applicator 20 is disposed on a rail 22 to move back and forth as operated by a linear controller 24, also operated under control of the motion control system 18. An imaging device 25 is also provided to capture images of a device to be coated, for example, a stent 26. In operation, the stent 26 is placed on the mandrel 12. Under control of the motion control system 18, using images obtained from the imaging device 25, the ink jet applicator 20 and the mandrel 12 are, respectively, linearly moved and/or rotated, to orient a portion of the stent 26 under the ink jet applicator 20 for receipt of a drop 28 of coating material. One of ordinary skill in the art will understand that a large number of drops would normally be deposited to coat a device. Only one drop, however, is shown for clarity.

The coating application system 10 may be one as is described in U.S. Pat. No. 6,645,547 to Shekalim et al., entitled "Stent Coating Device," and U.S. patent application Ser. No. 10/982,408, entitled "Method And Apparatus For Coating A Medical Device," the entire contents of each of which are incorporated herein.

The rail 22 is generally aligned in parallel to the rotating axis 14 about which the mandrel 12 rotates. In the coating system 10, it is important that the spatial relationship between the movement of the ink jet applicator 20 and the mandrel 12 be known so as to maintain the accuracy required for placement of the coating material on the stent 26. Accounting for this spatial relationship will be discussed below in more detail.

While a perfectly parallel alignment between the ink jet applicator 12, the rail 22, and the mandrel 12 is a goal, due to the limitations of the mechanical system and the build up of tolerances, the system 10 still has to be calibrated prior to use. Further details of the calibration procedure, in accordance with one embodiment of the present invention, will be discussed below.

Figure 2A:
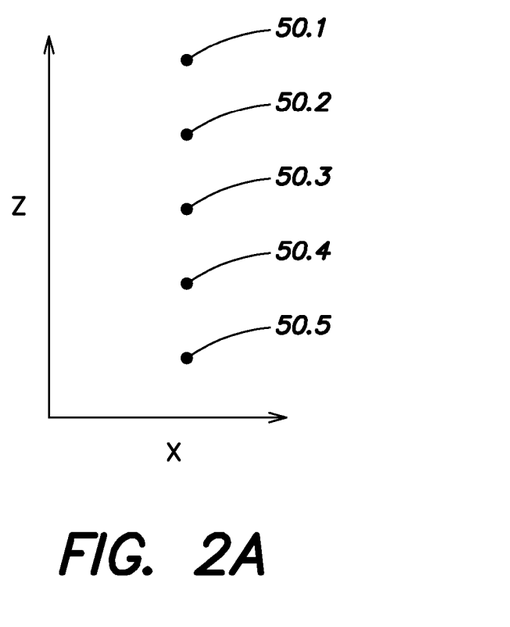
Figure 2B:
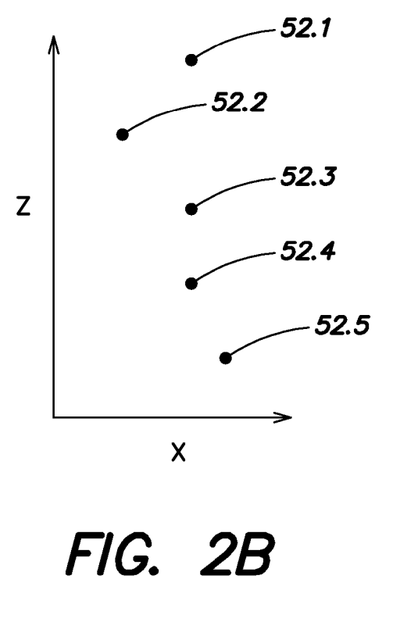

Conceptually, with reference to the graphs of FIGS. 2-A and 2-B, a Z-axis is oriented along the longitudinal length of the mandrel 12 while an X axis is oriented along the circumference of the mandrel 12. Thus, referring to FIG. 2-A, in a perfectly aligned system, a series of droplets 50.1-50.5 deposited at discrete locations along the Z axis would all line up with the same X value. It is possible, however, that, in actuality, a sequence of drops positioned by moving the ink jet applicator 20 along the rail 22, referring to FIG. 2-B with respect to drops 52.1-52.5, may have an X value that varies as the ink jet applicator 20 is moved along the rail 22. This deviation, or delta, in the X value may be due to the first point being at the incorrect Z location due to the inkjet head being in the wrong position, or due to travel inaccuracies as the inkjet applicator 20 moves along the rail 22. These variations can be compensated for by the use of calibration offsets stored in the motion control system 18 and by operation of the rotator 16 and linear controller 24. A system as in FIG. 2-B can be modified to operate as if it were a system operating as shown in FIG. 2-A.

Figure 3:
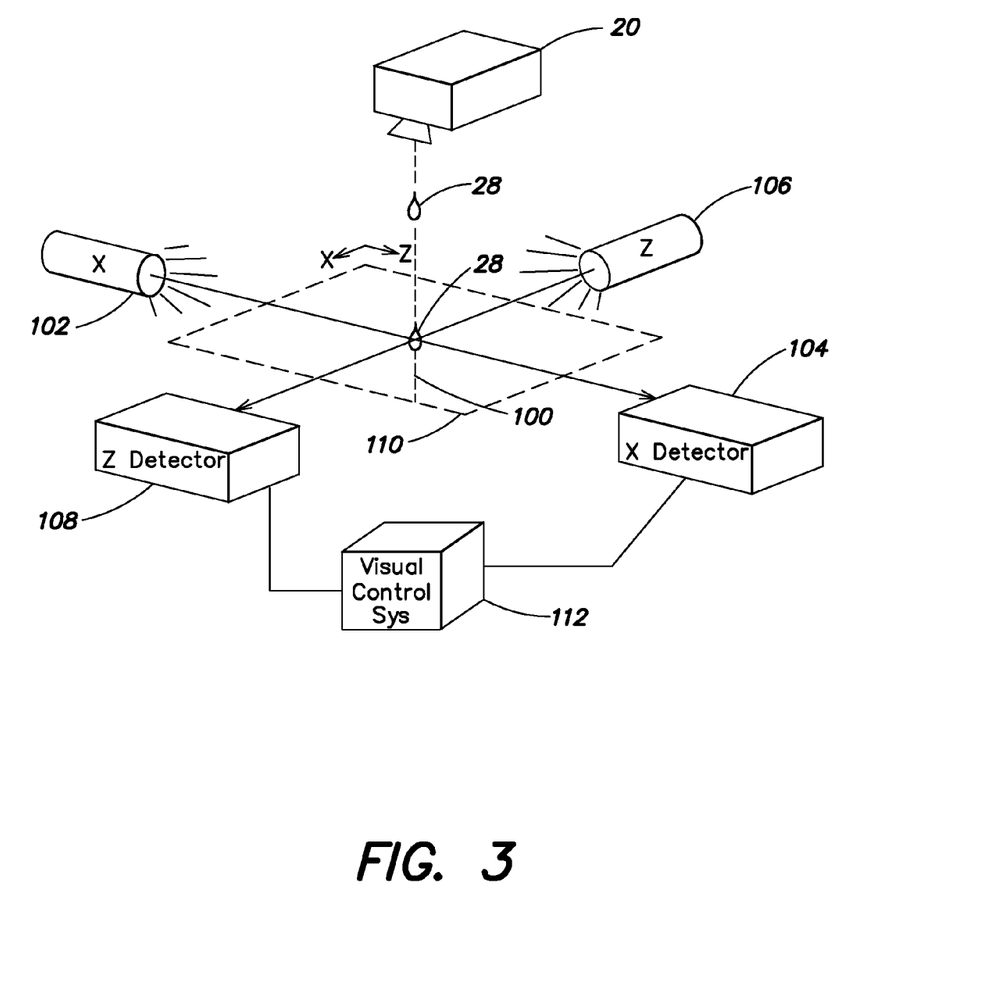
FIG. 3 is a schematic view of a position detecting system according to one embodiment of the present invention.

In accordance with one embodiment of the present invention, a location of a drop 28 ejected from the ink jet applicator 20 is captured in flight along a flight path 100 where the flight path 100 is shown by the dotted line in FIG. 3. A first light source 102 is positioned directly across from a first detector 104 and oriented such that the flight path 100 is between the first light source 102 and the first detector 104. Further, a second light source 106 is positioned opposite a second detector 108 also such that the flight path 100 passes between the second light source 106 and the second detector 108. Conceptually, a virtual line between the first light source 102 and the first detector 104, a virtual line between the second light source 106 and the second detector 108, and the flight path 100, are substantially orthogonal to one another where the lines between the first and second light sources 102, 106 and the respective detectors 104, 108 define a virtual plane 110. The first and second detectors 104, 108 are operated under control of a visual control system 112. The visual control system 112 may be a part of the motion control system 18 or separate from the motion control system 18 but in communication with it.

The first light source 102 and the first detector 104 and the second light source 106 and the second detector 108 are shown as being at right angles to one another in FIG. 3. It is envisioned that the angle between them could be something other than 90° and still function as is disclosed herein.

In one embodiment of the present invention, the first and second light sources 102, 106 are strobe lights coupled to the ink jet applicator 20. In addition, the first and second detectors 104, 108 are image capturing devices such as area CCD (Charge-Coupled Device) cameras with a resolution of, for example, 1,018×1,018 at eight bits. The strobe lights 102, 106 are triggered to flash a predetermined time after the drop 28 is ejected. In one embodiment, the predetermined time is set to place the drop 28 substantially in the plane 110 when the strobes flash at which time each of the first and second detectors 104, 108 captures an image of the drop 28.

According to one embodiment of the present invention, the image captured by the first detector 104 represents the location of the drop 28 in the X-axis and the image captured by the second detector 108 represents the location of the drop 28 in the Z axis.

The optical system comprising the first and second detectors 104, 108 is precalibrated so that a pixel size of the CCD detector is known, resulting in a distance measurement based on microns/pixel. Further, as part of the calibration process, the images captured by the first and second detectors 104, 108 are related to fixed locations in the coating system 10. In other words, a pixel in either of the images captured by the detectors 104, 108 identifies a specific location with respect to an origin of reference in the system 10.

Figure 4A:
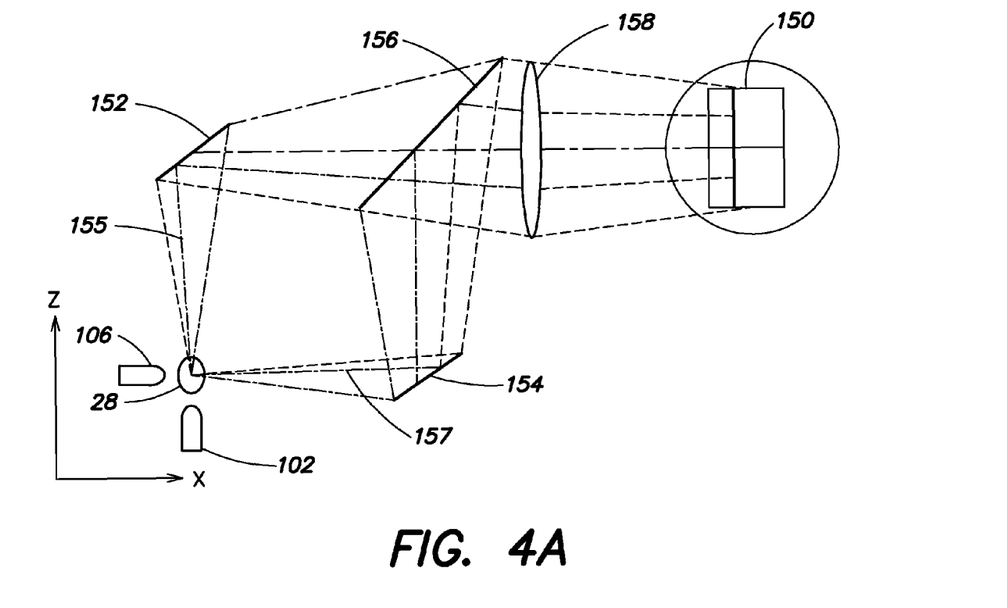

In an alternative embodiment of the present invention, as shown in FIG. 4-A, a single image capturing device 150 is used. FIG. 4-A is a schematic view of the system as viewed from above the ink jet applicator 20 and the drop 28 and looking down along the flight path 100. In this alternate embodiment, the first and second light sources 102, 106 are configured as shown in FIG. 3. A first folding mirror 152 is positioned opposite the first light source 102 and a second folding mirror 154 is located opposite the second light source 106. A beam splitter 156 is positioned to receive the light reflected by the first folding mirror 152 on a first side for light to travel through a pass-through portion of the beam splitter 156 and to receive the light reflected by the second folding mirror 154 on a second side for light to be reflected by a mirrored portion of the beam splitter 156. Each of the first and second light sources 102, 106 fills the full objective and field of view of the imaging device. The images of the drop 28 are directed to the respective sections by adjusting the first and second folding mirrors 152, 154 to direct the image, as shown by the first and second dotted lines 155, 157, to the respective portions of the beam splitter 156. The light reflected and passed through by the beam splitter 156 is directed toward the image capturing device 150. In an alternate embodiment, a microscope objective lens 158 is positioned between the beam splitter 156 and the image capturing device 150. It is contemplated that one of ordinary skill in the art will understand that the arrangement could be changed to have the first light fall on the mirrored portion of the beam splitter 156 and the second light pass through, with the detector arranged accordingly, and still function as described above.

The strobe lights 102, 106 are coupled to fire at the same predetermined time after the ejection of the drop 28 from the ink jet applicator 20. As a result of this configuration, two images of the drop at substantially a same point on the flight path 100 are captured from two different directions but in one image.

Figure 5:
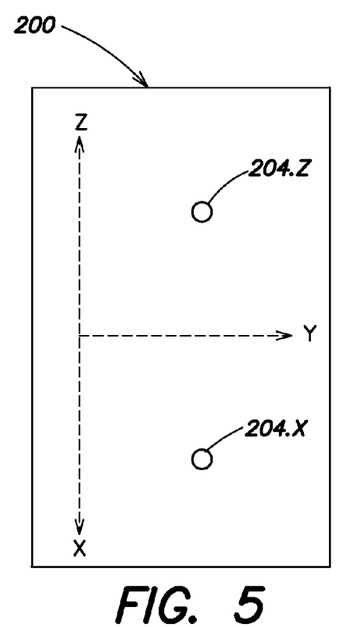
FIG. 5 is an image captured by an image capturing device in the system shown in FIG. 4-A.

In accordance with the embodiment shown in FIG. 4-A, an image 200 of the drop 28 in flight is captured as shown in FIG. 5. As is shown, two drop images 204.Z, 204.X of the drop 28 are captured. It should be noted that the dotted lines representing the X, Y, Z axes are depicted for explanatory purposes only and are not part of the captured image 200.

The drop image 204.Z represents the location of the drop 28 along the Z axis and the drop image 204.X represents the location of the drop 28 along the X axis. As the microns per pixel dimensions of the optical system are known, the number of vertical pixels "up" from the virtual Y-axis will represent the Z location of the drop 28 while the number of vertical pixels "down" from the virtual Y axis will measure the location of the drop 28 in the X axis.

Further, the number of horizontal pixels from the X-Z axis along the Y axis will measure the distance of the drop 28 from the tip of the ink jet applicator 20. As the strobes 102, 106 are triggered with a known time delay with respect to the release of the drop 28 from the ink jet applicator 20, and the drop location on the screen is known, then the relative location of the drop with respect to the tip can be calculated. The velocity at which the drop 28 is ejected from the ink jet 20 may change during system operation and/or when the jets are exchanged. The correct operation, i.e., drop velocity, can be verified by examination of the position of the drop image along the Y axis.

Figure 4B:
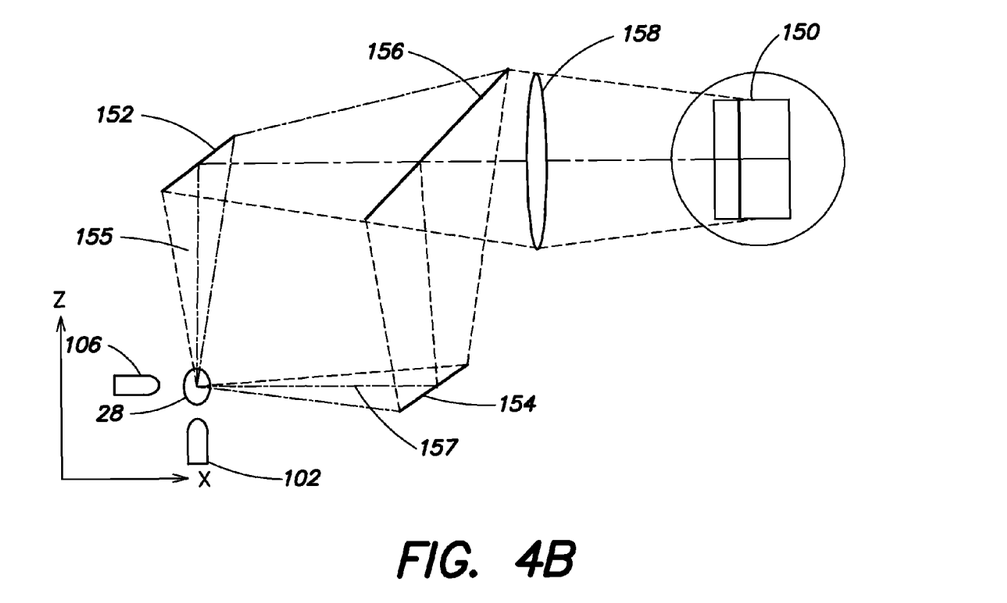

In yet another embodiment of the present invention, the drop image is directed to the center of the image detection field of the image capturing device 150 as shown in FIG. 4-B. The first and second folding mirrors 152, 154 are positioned to direct each image, as indicated by the lines 155, 157, to fall substantially in the center of the CCD field. As a result, the respective images for the Z and X axes will now fall on substantially the same portion of the image capturing device 150.

In operation, the embodiment shown in FIG. 4-B alternately samples to capture drop images for one direction and then drop images for the other direction. The first and second light sources 102, 106 are configured to fire separately instead of at the same time. As an example, the first light source 102 is triggered and a single image is captured to identify location along the X axis and then the second light source 106 is triggered to identify location along the Z axis. Each captured image only has one drop image and is separately analyzed.

The operation of the embodiment of FIG. 4-B separately triggers the first and second light sources 102, 106 to obtain alternate images. It is contemplated that other mechanisms for obtaining one image at a time may be implemented. In one example, the first and second light sources 102, 106 may be configured to fire at the same time but the light from one is blocked. A removable blocker may be placed between each light source and the flight path, between the flight path and each folding mirror, or between each folding mirror and the beam splitter. Alternately, each of the first and second light sources 102, 106 may be rotatable under control of the system to direct light away from the flight path when the other image is being captured. Further, each of the first and second folding mirrors may be rotatable under control of the system to direct the image away from the beam splitter when the image from the other direction is being captured. Still further, there may be one strobe signal but each of the first and second light sources has a separate power control and one is turned off when the other is firing or the path of the strobe signal to a light source is switched off when the other is being used. One of ordinary skill in the art will understand that there are many different mechanisms for assuring that an image from only one direction is captured.

Further, in the embodiments discussed above with respect to FIGS. 4-A and 4-B, the first light source 102 and the second light source 106 are at right angles to one another. It is envisioned that the angle between them could be something other than 90° and still function as is disclosed herein. One of ordinary skill in the art will understand how the first and second folding mirrors 152, 154 and the beam splitter 156 can be arranged to function as described above when the angle is other than a right angle.

Figure 6A:
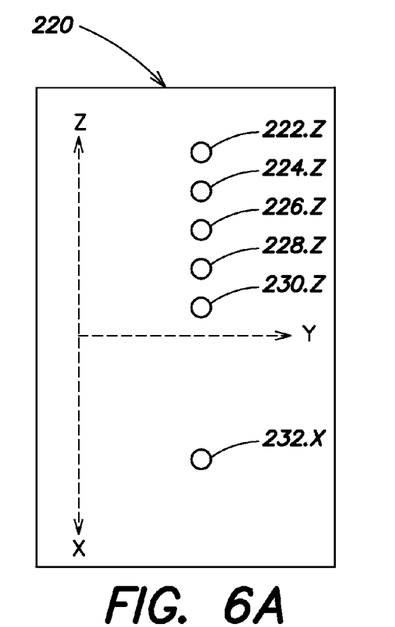
Figure 6B:
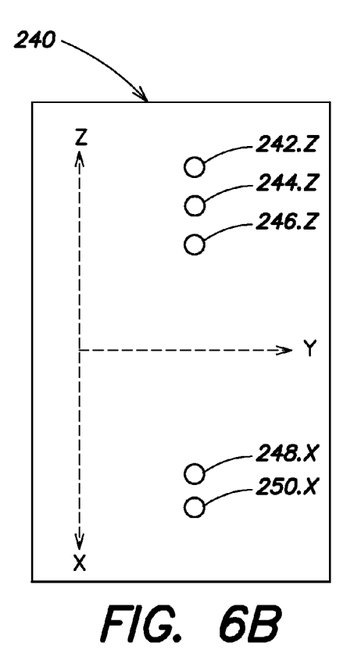

As shown in FIG. 6A, an image 220 captured for a series of drops 28 positioned sequentially along the Z axis would result in drop images 222.Z, 224.Z, 226.Z, 228.Z, and 230.Z at different points along the Z axis with only a single drop image 232.X representing that there was no substantial movement in the X axis as the ink jet applicator 20 moved along the rail 22. While it is not impossible to achieve the result as shown in FIG. 6A, it is more likely that an image 240 would be captured as shown in FIG. 6-B. As shown in FIG. 6-B, a number of drop images 242.Z, 244.Z and 246.Z represent images of drops that were captured as the ink jet applicator 20 moved along the rail 22. As shown in FIG. 6-B, one of the drops has a different X axis value as evidence by the capturing of drop images 248.Z and 250.Z in different locations along the X axis.

Figure 6C:
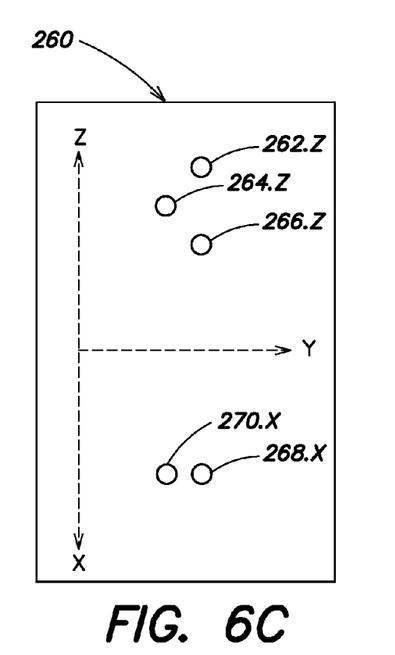

An image 260 may capture evidence of improper operation of the ink jet applicator 20, as shown in FIG. 6-C. A number of drop images 262.Z, 264.Z and 266.Z represent drops at various positions along the Z-axis. The drop images 268.X, 270.X indicate, however, that the drop corresponding to the image 270.X was not the same distance from the jet tip as the other drops. Assuming that the strobe lights were triggered at the same time for all of the drops and the drop velocity was set the same, the occurrence of drop images at different distances from the drop tip as shown in the image 260 may indicate another issue with the ink jet applicator 20.

Figure 9:
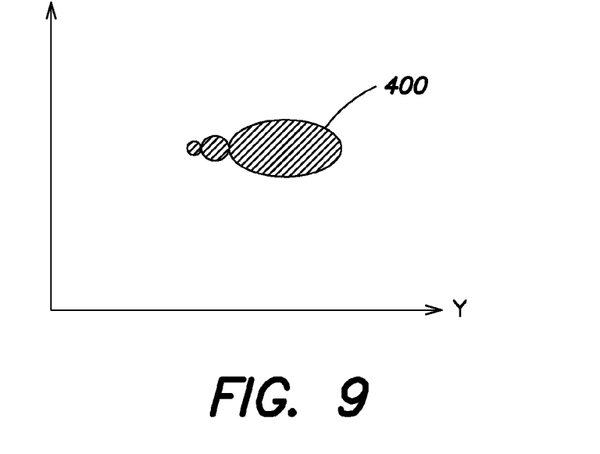
FIG. 9 is a representation of an actual drop image as captured in accordance with one embodiment of the present invention.

It should be noted that the representations of images captured in FIGS. 6A-6C are for explanatory purposes only and are not representative of an actual image that might be captured and, as described above, in one embodiment of the present invention each image that is captured and analyzed is for a particular X, Z coordinate. It may be that the image that is analyzed is an accumulation of a number of images captured for the specific X, Z coordinate in order to obtain an "average" position image by calculating a drop image "center of gravity." In one embodiment, an image analogous to a "multiple-exposure" image in the analog film realm is obtained. Images of a number of drops, ten in one embodiment, at a specific X,Z coordinate will be captured from each direction, and an accumulated drop image 400, as shown in FIG. 9, is obtained. The image may appear to be of a clean round drop or, similar to drop image 400, one with a tail or satellite. The drop's location is determined by this "visual averaging." The system reports if the variation or spread among the samples exceeds a predetermined threshold.

Alternatively, rather than multiply expose a number of drops on a single image, the system can be configured to capture one drop per image. The average position can then be determined as a result of determining the position in each image. If the variation or spread of determined locations is too great, the system may indicate this.

One of ordinary skill in the art would understand that analysis software can be obtained or written to identify a center of a drop image through known algorithms and image processing techniques. Such programs include the VisiSizer software suite available from Oxford Lasers of Littleton, Mass.

As an overview, the system 10 is built to align the linear jet applicator 20 with the mandrel 12. This alignment includes initially tuning or calibrating the system. As part of the initial tuning, the image detector 25 and the ink jet applicator 20 are calibrated to one another. The drop location verification system of the present invention is also calibrated to the jet applicator 20 and, therefore, by association, with the image detector 25. Subsequently, the drop location verification system can be used to evaluate the system and, if necessary, provide information to be used to re-calibrate the system.

Figure 7:
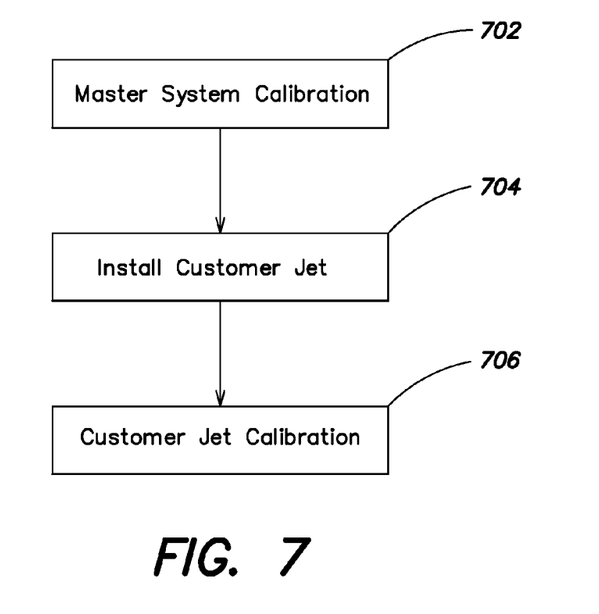
FIG. 7 is a flowchart of a method of calibration of a coating applicator.

The drop location verification system of the present invention operates, in one embodiment, as an adjunct to the calibration process of the overall coating system. When the system 10 is initially built it includes a master jet applicator that is used only in the factory for purposes of initial system calibration, step 702, as shown in FIG. 7. The calibration in step 702 synchronizes the image detector 25 and locations at which drops are placed and will be discussed in more detail below. Once the system 10 is calibrated, the master jet is removed and a customer jet is installed, step 704. The system is re-calibrated, step 706, often upon setup at the customer's location, to account for any variation that may have been introduced due to the jet head being replaced, the effects of being shipped, and/or to correct for any drift that may occur over the operational life of the system.

In general, the master calibration of the jet to the camera 25 establishes the relationship between drops ejected from the jet 20 for specific settings of the jet's location along the rail 22 and where those drops appear in the image captured by the camera 25. Generally, with reference to FIG. 10, a calibration procedure 2500 is performed on the system 10 as part of the system calibration step 702 to ensure accurate conversion of the CCD pixels in the camera 25 to the physical coordinates of the stent or device to be coated.

Figure 10:
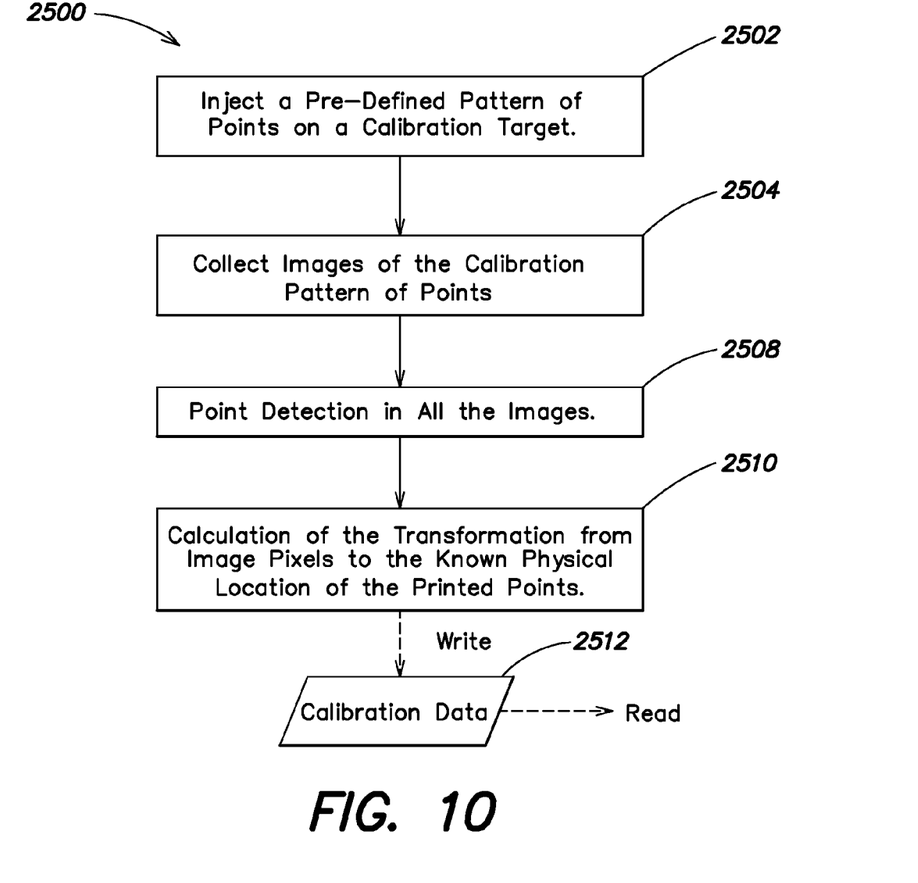
FIG. 10 is a flowchart of a calibration procedure.

A predefined pattern of points is injected on a calibration target, step 2502, using an injection material visible to the camera 25. These points are injected from known locations of the jet 20 along the rail 22. Images of these points are collected, step 2504. The positions in the images are detected, step 2508. A transformation from the image pixels to the known physical locations of the jet 20 is then calculated, step 2510. As it is known where the drops were fired from and where the drops' positions were detected, in one embodiment, a minimum square-error fitting process is performed and the parameters or calibration data of the transformation are calculated and saved, step 2512, for example in a calibration file, calib_file.

A mapping table that maps one or more pixels with respective jet locations may be maintained for the system. Alternatively, if the fitting or calibration operation determines that the behavior of the system can be expressed as a function or formula, then the formula would be stored and a mapping table would not be necessary.

In addition to the master calibration process 2500 between the camera 25 and the jet 20, initial X,Z locations for drops ejected from the jet 20 at known locations along the rail 22 are chosen and the respective locations detected by the drop location verification system are recorded. These initial locations are, therefore, linked to the master calibration information. Any subsequent change in X,Z measurements for drops from those same jet 20 positions on the rail 22 indicate changes in the system.

It should be noted that the locations from where drops detected by the location verification system are fired may or may not be the same as the drop locations used for the master calibration of the system described above. The locations of drops for detection by the drop verification system are chosen to be at least in the field of view of the detector 150 and would, therefore, also involve a predetermined timing delay from the firing of the drop for the firing of the strobes.

Figure 11:
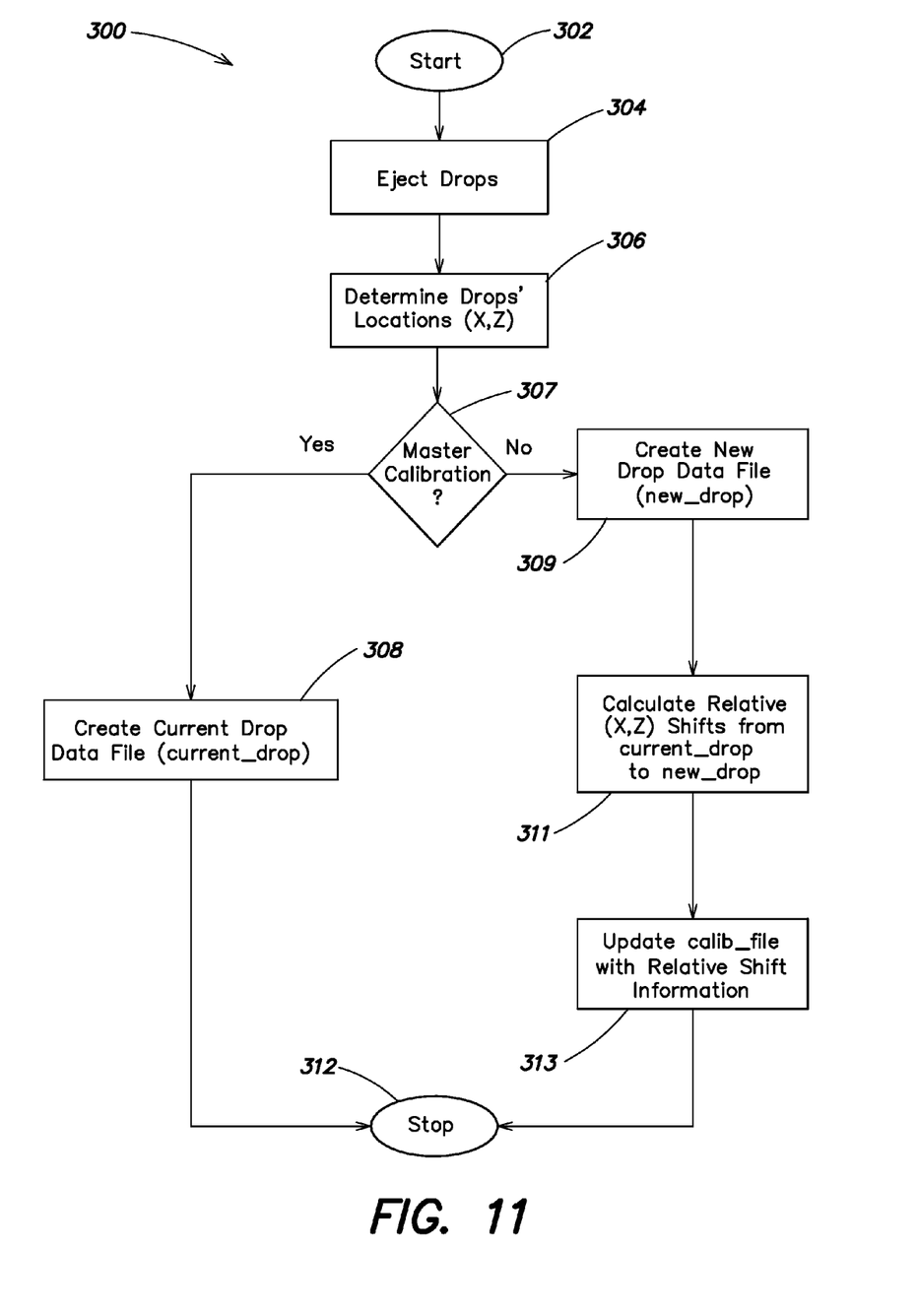
FIG. 11 is a flowchart of a method in accordance with one embodiment of the present invention.

Thus, a method 300 for calibrating the system, as shown in FIG. 11, is provided by one embodiment of the present invention. Initially, at step 302, the calibration procedure is started. Drops are ejected at predetermined locations by the ink jet applicator 20, i.e., the locations determined during master calibration for use in the verification process, at step 304. At step 306, each drop's location [X, Z] is determined. At step 307 it is determined whether or not this is master installation and calibration. If it is master installation and calibration, control passes to step 308 and a current drop data file, current_drop, is created. Once the current drop data file is complete then the operation is stopped, step 312.

Returning to step 307, if this operation is not master calibration, control passes to step 309 and a new drop data file, new_drop, is created. At step 311 any relative shifts in the X and Z locations for the drops' locations are calculated as a function of the current_drop file determined in step 308 compared to the new_drop file information determined in step 309. Once the relative shifts are determined in step 311, the calibration table data file, calib_file, is updated with the new relative shift information, step 313. If either of the relative shifts, in one direction, i.e., axis, or the other, exceeds a predetermined threshold, it may be that the system has lost too much accuracy and that it should be reviewed more thoroughly. This condition might occur if the apparatus is structurally compromised. The system would then indicate that the relative shift has exceeded the threshold and, possibly, halt operation until a more thorough process is completed.

Advantageously, the coating system 10 can be recalibrated or its current accuracy condition determined without having to use a calibration target or a master jet applicator. The drop location verification system will assist in the identification of any changes in the system's configuration. This is especially advantageous because the ink jet applicator 20 is a field replaceable unit and its replacement could affect calibration. Not only will the drop location verification system of the present invention check for system accuracy, it can also confirm proper operation of the ink jet applicator 20.

The control system 18, in one embodiment of the present invention, is a general purpose personal computer or computing device implementing one or more applications programs to control and interact with the rotator 16, the linear controller 24 and the visual control system 112. The control system 18 communicates with these devices through any one of many protocols as are known in the art. The computer may run an operating system such as Microsoft Windows, UNIX, Linux or Apple OS. The applications programs may be a combination of commercially available programs or programs written in any one of a number of available programming languages including, but not limited to, C, C++, JAVA, Perl and FORTRAN.

Figure 8:
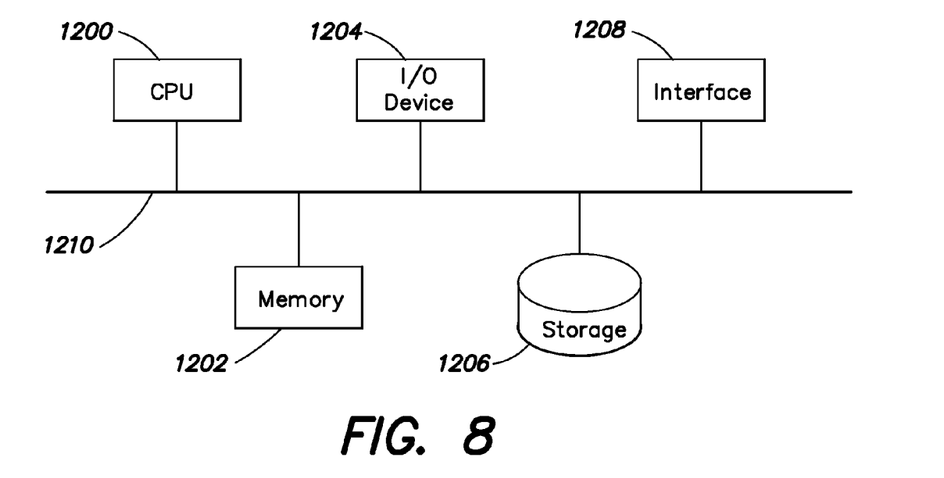
FIG. 8 is a block diagram of the functional parts of a computer system.

The computer, as above, can be any one of a number of different devices, however, these devices have some components and/or functionality in common irrespective of their relative technical complexities. As shown in FIG. 8, a computing device includes a central processing unit 1200, a memory 1202, an input/output device 1204, for example a keyboard, keypad or touch screen, storage 1206, for example a hard disk drive, and an interface 1208 for communicating to a network. A bus 1210 couples these devices to one another to allow communication between them.

Embodiments of the above-described invention may be implemented in either all software, all hardware, or a combination of hardware and software, including program code stored in a firmware format to support dedicated hardware. A software implementation of the above described embodiment(s) may comprise a series of computer instructions either fixed on a tangible medium, such as a computer readable media, e.g. diskette, CD-ROM, ROM, or fixed disk or transmittable to a computer system in a carrier wave, via a modem or other interface device. The medium can be either a tangible medium, including but not limited to optical or analog communications lines, or may be implemented with wireless techniques, including but not limited to microwave, infrared or other transmission techniques. The series of computer instructions whether contained in a tangible medium or a carrier wave embodies all or part of the functionality previously described herein with respect to the invention. Those skilled in the art will appreciate that such computer instructions can be written in a number of programming languages for use with many computer architectures or operating systems and may exist in machine executable format. Further, such instructions may be stored using any memory technology, present or future, including, but not limited to, semiconductor, magnetic, optical or other memory devices, or transmitted using any communications technology, present or future, including but not limited to optical, infrared, microwave, or other transmission technologies. It is contemplated that such a computer program product may be distributed as a removable media with accompanying printed or electronic documentation, e.g., shrink wrapped software, preloaded with a computer system, e.g., on system ROM or fixed disk, or distributed from a server or electronic bulletin board over a network, e.g., the Internet or World Wide Web.

Although various exemplary embodiments of the present invention have been disclosed, it will be apparent to those skilled in the art that changes and modifications can be made which will achieve some of the advantages of the invention without departing from the spirit and scope of the invention. It will be apparent to those reasonably skilled in the art that other components performing the same functions may be suitably substituted. Further, the methods of the invention may be achieved in either all software implementations, using the appropriate processor instructions, or in hybrid implementations that utilize a combination of hardware logic and software logic to achieve the same results.

What is claimed is:

1. A method of detecting an in-flight location of a drop in an inkjet system, the method comprising:
   ejecting a first drop from a first location, the first location having a predefined first axis coordinate and a predefined first axis threshold value associated therewith;
   capturing a first drop image of the first drop in flight;
   capturing a second drop image of the first drop in flight;
   determining a first axis coordinate of the first drop in the first drop image;
   calculating a first axis coordinate difference value between the determined first axis coordinate and the predefined first axis coordinate; and
   determining whether or not the calculated first axis coordinate difference value exceeds the first axis threshold value.

2. The method of claim 1, further comprising:
   capturing the first and second drop images not substantially at a same time.

3. The method of claim 1, further comprising:
   capturing the first and second drop images substantially at a same time.

4. The method of claim 1, further comprising:
   capturing the first and second drop images in a single captured image.

5. The method of claim 1, wherein a predefined second axis drop coordinate and a predefined second axis threshold value are associated with the predefined first location, the method further comprising:
   determining a second axis drop coordinate of the first drop in the second drop image;

calculating a second axis coordinate difference value between the second axis drop coordinate and the predefined second axis drop coordinate; and determining whether or not the calculated second axis coordinate difference value exceeds the predefined second axis threshold value.

6. The method of claim 5, further comprising:

indicating that the inkjet system is out of calibration if at least one of the calculated first and second axis coordinate difference values exceeds its respective predefined first and second axis threshold value.

7. The method of claim 5, further comprising:

if the calculated first axis and second axis coordinate difference values do not exceed, respectively, the predefined first and second axis threshold values, then modifying position control data for positioning an applicator from which the first drop is ejected, wherein the position control data is modified as a function of at least one of the calculated first axis and second axis coordinate difference values.

8. The method of claim 7, wherein modifying the position control data comprises at least one of:

updating a mapping of the predefined first and second axis coordinates to pixels in an image; and updating a formula that correlates the predefined first and second axis coordinates to pixels in an image.

9. A computer program product for use with an inkjet system coupled to a computer, the computer program product comprising computer readable program code for causing the computer to perform a method of detecting an in-flight location of a drop in the inkjet system, the method comprising:

ejecting a first drop from a first location, the first location having a predefined first axis coordinate and a predefined first axis threshold value associated therewith;

capturing a first drop image of the first drop in flight;

capturing a second drop image of the first drop in flight;

determining a first axis coordinate of the first drop in the first drop image;

calculating a first axis coordinate difference value between the determined first axis coordinate and the predefined first axis coordinate; and determining whether or not the calculated first axis coordinate difference value exceeds the first axis threshold value.

10. The computer program product of claim 9, the method further comprising:

capturing the first and second drop images not substantially at a same time.

11. The computer program product of claim 9, the method further comprising:

capturing the first and second drop images substantially at a same time.

12. The computer program product of claim 11, the method further comprising:

capturing the first and second drop images in a single captured image.

13. The computer program product of claim 9, wherein a predefined second axis drop coordinate and a predefined second axis threshold value are associated with the predefined first location, the method further comprising:

determining a second axis drop coordinate of the first drop in the second drop image;

calculating a second axis coordinate difference value between the second axis drop coordinate and the predefined second axis drop coordinate; and determining whether or not the calculated second axis coordinate difference value exceeds the predefined second axis threshold value.

14. The computer program product of claim 13, the method further comprising:

indicating that the inkjet system is out of calibration if at least one of the calculated first and second axis coordinate difference values exceeds its respective predefined first and second axis threshold value.

15. The computer program product of claim 13, the method further comprising:

if the calculated first axis and second axis coordinate difference values do not exceed, respectively, the predefined first and second axis threshold values, then modifying position control data for positioning an applicator from which the first drop is ejected, wherein the position control data is modified as a function of at least one of the calculated first axis and second axis coordinate difference values.

16. The computer program product of claim 15, wherein modifying the position control data comprises at least one of:

updating a mapping of the predefined first and second axis coordinates to pixels in an image; and updating a formula that correlates the predefined first and second axis coordinates to pixels in an image.

* * * * *